United States Patent [19]

Hohage

[11] Patent Number: 4,594,448

[45] Date of Patent: Jun. 10, 1986

[54] ESTERS OF VINYLCARBOXYLIC ACIDS

[75] Inventor: Heinz-Jüergen Hohage, Muehltal, Fed. Rep. of Germany

[73] Assignee: Rohm GmbH Chemische Fabrik, Darmstadt, Fed. Rep. of Germany

[21] Appl. No.: 764,010

[22] Filed: Aug. 9, 1985

[30] Foreign Application Priority Data

Aug. 18, 1984 [DE] Fed. Rep. of Germany ....... 3430446

[51] Int. Cl.$^4$ ...................... C07C 69/52; C08F 32/00
[52] U.S. Cl. ..................................... 560/220; 526/309
[58] Field of Search ......................... 560/220; 526/309

Primary Examiner—Paul R. Michl
Assistant Examiner—Alex H. Walker
Attorney, Agent, or Firm—Oblon, Fisher, Spivak, McClelland & Maier

[57] ABSTRACT

Esters of vinylcarboxylic acids having the formula (I):

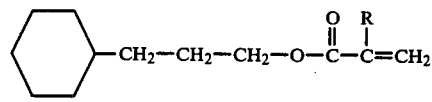

wherein R is H, or methyl.

The esters of the present invention are useful as monomers which can be used to prepare polymers which are used to prepare dental materials.

4 Claims, No Drawings

ESTERS OF VINYLCARBOXYLIC ACIDS

BACKGROUND OF THE INVENTION

1. Field of the Invention

The present invention relates to esters of vinylcarboxylic acids and their use as monomers which can be polymerized or copolymerized with other monomers.

2. Description of the Background

A large number of monomers polymerizable by radical polymerization are presently available. For example, derivatives of acrylic acid and methacrylic acid, particularly the esters of these acids, play an important role in the polymer manufacturing industry. Thus, with methyl methacrylate in particular, a whole class of plastics has been developed which has found extensive application in many areas of technology and industry. See R. Vieweg and F. Esser, 1975, "Kunststoff-Handbuch, Band IX, Polymethacrylat", pub. C Hanser Verlag. In addition to methyl methacrylate, mumerous other acrylic and methacrylic based compounds serve as monomeric starting compounds for polymers and copolymers. See J. Brandrup and E. H. Immergut, 1975, "Polymer Handbook, 2nd Ed.", pub. Wiley Interscience.

The properties of the polymers prepared are, of course, influenced by the choice of monomers and by the method of polymerization. However, despite the already existing classes of polymers, a need continues to exist for new polymers which are easily produced and which have particular utilities because of their molecular structure. For example, at present a strong need exists for polymers which have properties which befit a use as a dental material. However, in general, a need also continues to exist for new monomers and the polymers derived therefrom which are better adapted to specific requirements profiles for plastics than monomers and polymers already on the market.

SUMMARY OF THE INVENTION

Accordingly, it is an object of the present invention to provide esters of vinylcarboxylic acids which can be easily polymerized or copolymerized with other monomers.

It is an object of this invention to provide polymers or copolymers which contain the above esters of vinylcarboxylic acids as monomers.

According to the present invention, the foregoing and other objects are attained by providing esters of vinylcarboxylic acids of the formula (I):

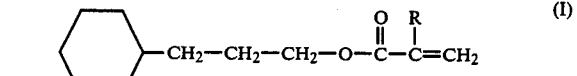

wherein R is H, or methyl.

DETAILED DESCRIPTION OF THE PREFERRED EMBODIMENTS

Despite the large number of known acrylate and methacrylate monomers and polymers derived therefrom, there is a constant demand for new monomers capable of producing polymers having specific properties or of influencing the properties thereof. However, despite the ability of skilled artisans to approximate the behavior and effects of a given monomer on a polymer, such projections are attended with much uncertainty. The single exception to this appears to involve polymers derived from monomers which are strictly homologous compounds.

It has now been discovered that monomers of the formula (I):

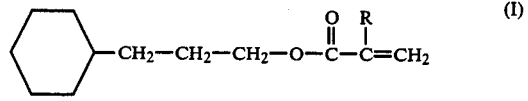

wherein R is H, or methyl can be used advantageously in the production of homopolymers or copolymers.

The polymers of the present invention are used advantageously in the production of dental material compositions.

The esters of the formula (I) can be prepared by known methods. For example, the esters may be conveniently prepared by reacting derivatives of acrylic or methacrylic acid, having the formula (II):

wherein X is a suitable leaving group, such as, for example, chlorine or bromine or the group

and wherein R is as defined above, with 3-cyclohexylpropanol, with the reaction optionally being carried out in the presence of an acid acceptor. See, for example, U.S. Pat. No. 1,951,782 which is incorporated by reference herein in the entirety.

Alternatively, the esters of the present invention may be prepared by reacting metal salts, particulary potassium or silver salts, of acrylic acid or methacrylic acid, with 3-cyclohexylpropyl halides, particularly the chloride or the bromide, or with tosylates; or by esterifying the acrylic acid or methacrylic acid with 3-cyclohexylpropanol, preferably with the water formed being bound by dehydrating agents; or preferably by the transesterification of lower esters of acrylic acid or methacrylic acid, of the formula (III):

wherein R' is one of the substituents defined above for R of formula I, and R" is methyl, ethyl, propyl, or butyl, with the transesterification being carried out in the presence of transesterification catalysts. See: H. Rauch-Puntigam and Th. Voelker, 1967, "Acrylund Methacrylverbindungen" pub. Springer Verlag, pp. 36–40; and U.S. Pat. No. 2,138,763.

Candidates for transesterification catalysts include, e.g., basic catalysts such as alkali alcoholates, see, for example, Swiss pat. 239,750, acid catalysts such as p-toluenesulfonic acid or sulfuric acid, see Brit. Pat. Nos. 461,979 and 906,005, or orthotitanic acid esters, see Brit. Pat. Nos. 960,005 and 962,928.

Advantageously the reactions are carried out in the presence of a polymerization inhibitor such as quinone, benzothiazine, phenols, methylene blue, aromatic amines, e.g. diphenylamine, or nitro compounds, and possibly in the presence of copper salts or iron salts. The amounts of inhibitors which may be used are generally on the order of magnitude of 0.01–0.1 wt. %, based on the weight of the starting ester in the transesterification. See "Ullmanns Encyklopaedie der techn. Chemie, 4. Auflage, Bd. 15", 1978, pp. 256 ff, pub. Verlag Chemie. Particular examples of polymerization inhibitors are hydroquinone monomethyl ether and hydroquinone.

The polymerization of the ester monomers of the present invention is advantageously conducted using free radical polymerization. For example, the polymerization technique of Rauch-Puntigam, supra may be used. In such a technique, approximately three parts of polymer, mostly "pearl" polymers with about 0.17 of dibenzoylperoxide added, are mixed to form a slurry with one part of monomer. The polymer is preferably polymethyl methacrylate while the monomer is a mixture of methylmethacrylate and the designated monomer. According to such a process, one would use the vinylcarboxylic acid esters of the present invention. Preferably, the weight ratio of the methyl methacrylate to the present esters used is about 9:1.

However, as noted previously, the monomers of the present invention may be homopolymerized or copolymerized with any suitable ethylenically unsaturated monomer to produce a copolymer. While any ethylenically unsaturated monomer can be used, particularly useful are acrylic or methacrylic acid or ester derivatives thereof. However, the co-monomers may be chosen as requirements vary. Nevertheless, also worth mentioning as co-monomers are the esters and amides of acrylic acid and methacrylic acid, acrylonitrile, methacrylonitrile, styrene and the alkylated derivatives of styrene, vinyl ethers and vinyl esters.

As noted, according to formula (I) of the present invention, R may be H, or methyl.

The present invention will now be further illustrated by certain examples and references which are provided for purposes of illustration only and are not intended to limit the present invention.

EXAMPLE 1

In a 4 liter three-neck round bottomed flask equipped with a thermometer, a reflux condenser with distillation attachment, and a stirrer, 852 g (6 mol) 3-cyclohexyl-1-propanol, 1800 g (18 mol) methyl methacrylate, 0.18 g p-methoxyphenol, and 26 g isopropyl titanate were heated to boiling, while passing air through the mixture, and a methanol/methyl methacrylate azeotrope was drawn off, until complete conversion was achieved (c. 3.5 hr). The excess methyl methacrylate was removed in a rotary evaporator, and the residue was distilled. 3-Cyclohexylpropyl methacrylate was obtained in 91.5% yield. Purity as determined by gas-chromatography: >98% B.p. (0.8 mm):88° C. $n_D^{20}$:1.464.

EXAMPLE 2

Completely analogously to Example 1, the 3-cyclohexylpropyl acrylate was prepared, by using ethyl acrylate instead of methyl methacrylate. Reaction time:3 hr. Yield: 85%. Purity by GC:>98%. B.p. (0.9 mm):85° C. $n_D^{20}$:1.4636. $d_4^{20}$:0.9480.

EXAMPLE 3

Use in dental materials

A pearl polymer consisting of 92 parts by weight of methylmethacrylate and 8 parts by weight of 3-cyclohexylpropyl methacrylate is used. Central pearl size $Z_2$ is 90 μm. The polymer is converted to a denture as described in Ullmann's Encyclopaedie der Techn. Chemie, 4. Auflage Vol. 10, pp 8 and 9, publ. Verlag Chemie. When triturized with 0.5 parts by weight of methylmethacrylate the material rapidly becomes non-sticky (within ca. 3 minutes) and stays ready for use for approximately one hour.

Having now fully described the present invention, it will be apparent to one of ordinary skill in the art that many changes and modifications can be made thereto without departing from the spirit or scope of the invention as set forth herein.

What is claimed as new and desired to be secured by Letters Patent of the United States is:

1. Esters of vinylcarboxylic acids having the formula (I):

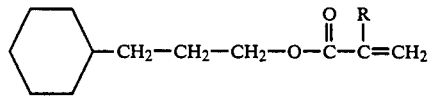

wherein R is H, or methyl.

2. A homopolymer or copolymer comprising as at least one of the repeating monomer units, a monomer of the formula (I):

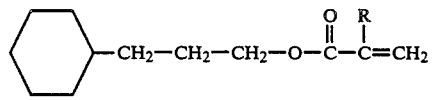

wherein R is H, or methyl.

3. The homopolymer or copolymer according to claim 2, produced by free radical polymerization.

4. The copolymer of claim 2, which further comprises as a repeating monomer unit, a monomer selected from the group consisting of esters and amides of acrylic acid and methacrylic acid, acrylonitrile, methacrylonitrile, styrene and the alkylated derivatives of styrene, vinyl esters and vinyl ethers.

* * * * *